(12) United States Patent
Okada et al.

(10) Patent No.: US 6,709,634 B1
(45) Date of Patent: Mar. 23, 2004

(54) AUTOMATIC ANALYTICAL INSTRUMENT (75) Inventors: Satoru Okada, Akashi (JP); Tadahiro Takami, Kakogawa (JP); Motoki Koyama, Kobe (JP); Katsushi Yano, Takamatsu (JP); Koichi Miyake, Takamatsu (JP)

(73) Assignees: Sysmex Corporation, Hyogo (JP); Ryusyo Industrial Co., Ltd., Osaka (JP)

( * ) Notice: Subject to any disclaimer, the term of this patent is extended or adjusted under 35 U.S.C. 154(b) by 0 days.

(21) Appl. No.: 09/568,804

(22) Filed: May 11, 2000

(30) Foreign Application Priority Data

May 11, 1999 (JP) .............................. 11-130666
Apr. 28, 2000 (JP) ....................... 2000-130369

(51) Int. Cl.$^7$ .............................................. G01N 35/04
(52) U.S. Cl. ............................ 422/64; 422/65; 436/47; 436/48
(58) Field of Search .............................. 422/63, 64, 65, 422/67, 73, 100; 436/43, 47, 48, 49, 50, 54, 55, 174, 180

(56) References Cited

U.S. PATENT DOCUMENTS

| 5,051,238 A | * | 9/1991 | Umetsu et al. | 422/64 |
|---|---|---|---|---|
| 5,242,659 A | * | 9/1993 | Wurschum | 422/65 |
| 5,482,861 A | * | 1/1996 | Clark et al. | 436/48 |
| 5,501,838 A | | 3/1996 | Ootani et al. | |
| 5,587,129 A | | 12/1996 | Kurosaki et al. | |
| 5,876,668 A | * | 3/1999 | Kawashima et al. | 422/64 |
| 5,882,594 A | * | 3/1999 | Kawaguchi et al. | 422/64 |

FOREIGN PATENT DOCUMENTS

| JP | 7000935 Y2 | 1/1995 |
|---|---|---|
| JP | 8094636 A | 4/1996 |

* cited by examiner

Primary Examiner—Jeffrey Snay
(74) Attorney, Agent, or Firm—Birch, Stewart, Kolasch & Birch, LLP (57) ABSTRACT An automatic analytical instrument comprising a plurality of specimen tubes to store specimens, a plurality of storage tubes to store a part of the specimens contained in the specimen tubes by dispensing, a first dispensing unit to dispense the specimens contained in the specimen tubes into the storage tubes, a first turning table to hold a plurality of the storage tubes and transfer them by revolution, a plurality of analytical tubes to store a part of the specimens contained in the storage tubes by dispensing, a second dispensing unit to dispense the specimens contained in the storage tubes into the analytical tubes, a second turning table to hold a plurality of the analytical tubes and transfer them by revolution, an analytical unit to analyze the specimens contained in the analytical tubes, a transfer unit to transfer the analytical tubes held in the second turning table to the analytical unit, an delivering unit to deliver the analytical tubes after analysis is completed, a tube supply unit to supply the storage tubes and the analytical tubes which fall naturally into the first turning table and the second turning table, and a control unit to control dispensing by the first dispensing unit and the second dispensing unit, revolution by the first turning table and the second turning table, analysis by the analytical unit, transfer by the transfer unit, delivery by the delivering unit and supply by the tube supply unit.

10 Claims, 9 Drawing Sheets

AUTOMATIC ANALYTICAL INSTRUMENT

CROSS-REFERENCE TO RELATED APPLICATIONS

This application is related to Japanese patent applications No. Hei 11(1999)-130666 filed on May 11, 1999 and No. Hei 2000-130369 filed on Apr. 28, 2000 whose priorities are claimed under 35 USC §119, the disclosure of which is incorporated herein by reference in its entirety.

BACKGROUND OF THE INVENTION

1. Field of the Invention:

This invention relates to an automatic analytical instrument and, more particularly, to an automatic analytical instrument that dispenses specimens such as blood and urine, and test reagents into storage tubes such as cuvettes and test tubes, allows to react in a reaction unit and optically measures various constituents contained in such specimens at a photometric unit.

2. Description of the Related Art:

In general a blood coagulation test or an immunoassay requires analysis of a plurality of items with respect to specimens. For instance, the blood coagulation test requires measurement of various items ranging from basic items including PT (prothrombin time), APTT (Activated Partial Thromboplastin Time), and Fibrinogen to complex factors including TTO (Thrombo Test), HPT (Hepaplastin test), chromogenic agents, FDP (Fibrinogen and fibrin degradation products) and Ddimer by the use of nephelometery.

Some of the above items include those that have varying reaction conditions such as reaction time and reagent addition time and those that have to use separate photometric units. An analytical instrument that can analyze a number of the above items by the use of random access is desired, but to realize such an instrument, an advanced controlling system is required. Therefore, in recent years, more and more analytical instruments use disposable specimen tubes for reaction and measurement. The reason behind this is that using disposable tubes can dispose of a mechanism for washing the reaction unit and save washing time and that no controls for the above procedure is required.

An advanced automatic analytical instrument using disposable tubes is disclosed in a Japanese Laid-Open Patents Publication No. Hei 8(1996)-9463. This automatic analytical instrument uses cuvettes (storage tubes) as disposable tubes, transfers these cuvettes one by one from a specimen supply unit, via a reagent supply unit, to a reaction measurement unit following a process flow and conducts each test in each cuvette. Since this analytical instrument can conduct individual tests for each specimen, it is perfect for the blood coagulation test that has items requiring various reaction conditions and varying reaction time.

In addition, this analytical instrument can conduct reflect measurements, that is, measure specific items or other measured items again depending on the test results. Since at the time of measurement, first, specimens are distributed by being poured into cuvettes once and distributed by pouring into other cuvettes and then measured, the specimens can be stored in the cuvettes. Accordingly, this automatic analytical instrument enables reflect tests to be conducted without storing specimens of a blood collection tube in a sampler and the like until the test results are obtained and in this regard it is innovative.

However, it is required that in this automatic analytical instrument cuvettes are supplied one by one. In other words, cuvettes are supplied to one by one by a cuvette supplying means (transferring means) disclosed in Japanese Laid-Open Utility Model Publication No. Hei 3(1991)-25157 so that a tube catcher (a turning member) may receive it. It is hard to make the supply speed faster than a certain speed owing to mechanical restrictions. Yet, it is undesirable to furnish this automatic analytical instrument with a plurality of cuvette supplying means from the viewpoint of costs and space.

SUMMARY OF THE INVENTION

The objective of this invention is to provide an automatic analytical instrument that can supply simple tubes to fixed positions in a faster and easier way for the purpose of improving the performance of the automatic analytical instrument employing simple tubes such as cuvettes.

This invention provides an automatic analytical instrument comprising a plurality of specimen tubes to store the specimens, a plurality of storage tubes to store a part of the specimens contained in the specimen tubes by dispensing, a first dispensing unit to dispense the specimens contained in the specimen tubes into the storage tubes, a first turning table to hold a plurality of the storage tubes and transfer them by revolution, a plurality of analytical tubes to store a part of the specimens contained in the storage tubes by dispensing, a second dispensing unit to dispense the specimens contained in the storage tubes into the analytical tubes, a second turning table to hold a plurality of the analytical tubes and transfer them by revolution, an analytical unit to analyze the specimens contained in the analytical tubes, a transferring unit to transfer the analytical tubes held in the second turning table to the analytical unit, an delivering unit to deliver the analytical tubes after analysis is completed, a tube supply unit to supply the storage tubes and the analytical tubes to the first turning table and the second turning table into which they fall naturally, and a control unit to control dispensing by the first dispensing unit and the second dispensing unit, revolution by the first turning table and the second turning table, analysis by the analytical unit, transfer by the transfer unit, delivery by the delivering unit and supply by the tube supply unit.

Blood collection tubes, for instance, which can stand on racks, are desirable as specimen tubes. It is desired that the identical tubes be used for storage tubes and analytical tubes and so can be interchangeable, and cuvettes that can be held in a turning table are often used as such. Here, cuvettes mean small-sized tubes storing specimens and reagents for the purpose of observing reactions and conducting analysis and there are no restrictions in respect of shapes. A cylinder with a bottom, a rectangular tube with a bottom, a inverted circular cone, an inverted pyramid, and a combination of the above are desirable and are often used. There are no restrictions with respect to the materials of cuvettes, either, but transparent plastic materials are desirable. Cuvettes can be either washed and reused or thrown away after being used.

The first turning table and the second turning table can respectively hold a plurality of storage tubes and a plurality of analytical tubes in a plurality of holding holes provided on the circumferences and can transfer them by their revolution. The first dispensing unit, the second dispensing unit, the analytical unit, the transferring unit and the delivering unit are provided at prescribed positions in this automatic analytical instrument and composed of known constitution and mechanism.

The tube supply unit supplies storage tubes and analytical tubes to the first turning table and the second turning table, respectively, without using any of variety of means, such as grasping, moving and then letting them go, by making good use of the weight of tubes and dropping them naturally.

The control unit controls at least, dispensing by the two dispensing units, revolution by the two turning tables, analysis by the analytical unit, transfer by the transferring unit, delivery by the delivering unit and supply by the tube supplying unit. This control unit consists of a CPU installed inside the main body of this instrument, various control circuits and various driving motors.

It is desirable that the two turning tables be placed in concentric circles having different diameters. If they are provided as above, installation space and driving motors can be cut down on and miniaturization of the instrument and reduction of cost can be realized.

DESCRIPTION OF THE PREFERRED EMBODIMENTS

The tube supply unit comprises a storage part, a chute and an allocation part. The storage part stores a plurality of storage tubes and/or analytical tubes. The chute is placed below the storage part, and aligns the tubes in the storage part, making them slide down. The allocation part is laid below the chute and holds the tubes that slid down the chute and then supplies them to the first turning table and the second turning table into which they fall naturally.

If the tube supply unit is composed as above, it can supply the storage tubes and/or analytical tubes to the first turning table and/or the second turning table by making good use of the weight of the tubes and dropping them naturally without using any of a variety of means such as grasping them, transferring them and then letting them go.

The following is a more specific constitution of the tube supply unit. It comprises the storage part that is composed of a hopper having a hole for passing tubes in the lower part, the chute that is composed of a guide rail running diagonally downwardly from the hole for passing tubes in the hopper and is capable of swinging up and down and a shooter connected with the lower part of the guide rail and running diagonally downwardly from it, the allocation part that is composed of the first guide body provided diagonally below the chute, which is capable of swinging from side to side and having a hole for passing tubes in its center and the second guide body provided fixedly diagonally below the first guide body and having a portion for holding tubes in its center and one hole for passing tubes, respectively, at the sides.

If the tube supply unit is composed as above, a number of aligned storage tubes and/or aligned analytical tubes put in the hopper then slide down the chute from the hole for passing tubes in the hopper by way of the guide rail. A front-running tube is held by the hand for holding tubes in the second guide body after it partially passes the hole for passing tubes in the first guide body. When the first guide body swings either to the left or to the right and its hole for passing tubes and one hole for dropping tubes in the second guide body overlap, this tube drops naturally through the hole for passing tubes and the hole for dropping tubes and lands in one of the holding holes in either the first turning table or the second turning table laid below.

It is recommended that the two turning tables and the tube supply unit should be placed so that one of the holding holes in the first turning table and in the second turning table may be situated just below one of the holes for dropping tubes in the second guide body and that the other holding hole in the first turning table and in the second turning table is situated just below the other hole for dropping tubes in the second guide body.

It is desirable that the control unit can further control the swing of the guide rail and the swing of the first guide body. If it is constituted as above, it can freely control revolution of the first turning table and/or the second turning table and the free fall of the storage tubes and/or analytical tubes.

It is desirable that in addition to the above the automatic analytical instrument of the invention should have a third turning table to hold a plurality of reagent storage tubes for the purpose of storing various reagents and to transfer them by revolution. It is more desirable that together with the first turning table and the second turning table the third turning table should be provided in concentric circles having different diameters.

It is desirable that the automatic analytical instrument of the invention should have a heating/cooling unit that heats and/or cools at least one of the first turning table, the second turning table and the third turning table and that it be constituted so that the control unit may further control the heating/cooling unit. Here, an electrical heater is used as the heating unit and a water cooling mechanism is used as the cooling unit. If the automatic analytical instrument is constituted as above, by heating or cooling a desired turning table the tubes held by the turning table can be heated and/or cooled.

Hereinafter, an explanation is made as to one embodiment of the invention with reference to the drawings. This does not impose any restrictions on the invention.

Shown in FIG. 1 through FIG. 4, an automatic analytical instrument P of the invention comprises a plurality of specimen tubes 2, a plurality of storage tubes 4, a first dispensing unit 6, a first turning table 8, a plurality of analytical tubes 10, a second dispensing unit 12, a second turning table 14, an analytical unit 16, a transferring unit 18, an delivering unit 20, a tube supply unit 22 and a control unit 24.

The specimen tubes 2 are blood collection tubes that contain plasma as specimens, and stand in a sample rack 28 set in a right sampler tank 26 situated in the front of and to the right of this automatic analytical instrument P. The storage tubes 4 are supplied by the tube supply unit 22 and store a part of the specimen contained in the specimen tubes 2 by distributing by pouring the specimen into them. The first dispensing unit 6 is designed to dispense the specimen contained in the specimen tubes 2 into the storage tubes 4 on the first turning table 8 and comprises a first pipette 30 and a first arm 32 to move the first pipette 30 horizontally and vertically. The first turning table (primary taking in loader) 8 is shaped like a ring and holds a plurality of storage tubes 4 in a plurality of holding holes 9 provided on its circumference and transfers them by revolution. The first turning table 8 is designed to take the specimen contained in the specimen tubes 2 into the storage tubes 4.

The analytical tubes 10 are designed to be supplied by the tube supply unit 22 and store a part of the specimens contained in the storage tubes 4 by distributing by pouring the specimens into them. The second dispensing unit 12 is a unit that dispenses the specimens contained in the storage tubes 4 on the first turning table 8 into the analytical tubes 10 on the second turning table 14 and comprises a second pipette 34 and a second arm 36 to move the second pipette 34 horizontally and vertically. The second turning table (heating loader) 14 is shaped like a ring having a diameter larger than the first turning table 8 and holds a plurality of the analytical tubes 10 in a plurality of holding holes 15 on its circumference and transfers them by revolution. The second turning table 14 is heated to be 37±0.5° C. for the purpose of heating the analytical tubes 10.

The storage tubes 4 and the analytical tubes 10 are identical and comprise a cylindrical main body having a bottom and an upper flange whose diameter is larger than that of the main body and made of a disposable, transparent plastic cuvette.

The analytical unit 16 is a unit that analyzes the specimens contained in the analytical tubes 10 and comprises a catcher 17 to hold the analytical tubes 10, a heating table 38 to heat the analytical tubes 10 and a detector 90. The transferring unit 18 is a unit that transfers the analytical tubes 10 held in the second turning table 14 to the analytical unit 16 and comprises a catcher 19 to hold the analytical tubes 10.

The delivering unit 20 is a unit that delivers the analytical tubes 10 after analysis and comprises a catcher 21 to hold the analytical tubes 10 and a belt 40 to convey the analytical tubes 10 to the vent 42. The tube supply unit 22 is a unit that supplies the storage tubes 4 and analytical tubes 10 to the first turning table 8 and the second turning table 14 into which they fall naturally.

The control unit 24 controls dispensing by the first dispensing unit 6 and the second dispensing unit 12, revolution of the first turning table 8 and the second turning table 14, analysis of the analytical unit 16, transfer of the transfer unit 18, delivery of the delivering unit 20 and supply by the tube supply unit 22. The control unit 24 contains a CPU, various driving motors and the like provided in the main body of the automatic analytical instrument P.

In addition to the above, this automatic analytical instrument P has a third turning table (holder of diluted solution and clearing fluid) 46 to hold a plurality of tubes storing reagents 44 for the purpose of storing various reagents, diluted solutions and clearing fluids and to transfer them by revolution. The third turning table 46 has a diameter smaller than that of the first turning table 8 and is provided in a concentric configuration together with the first turning table 8 and the second turning table 14. Each of the first turning table 8, the second turning table 14 and the third turning table 46 can independently be revolved by one driving motor.

Various reagents and the like stored in the tubes storing reagents 44 in the third turning table 46 can be put into the storage tubes 4 held by the first turning table 8 and/or the analytical tubes 10 held by the second turning table 14 by the use of a third pipette 50 capable of moving back and forth from side to side horizontally, attached to a third arm 48.

Figure 1:
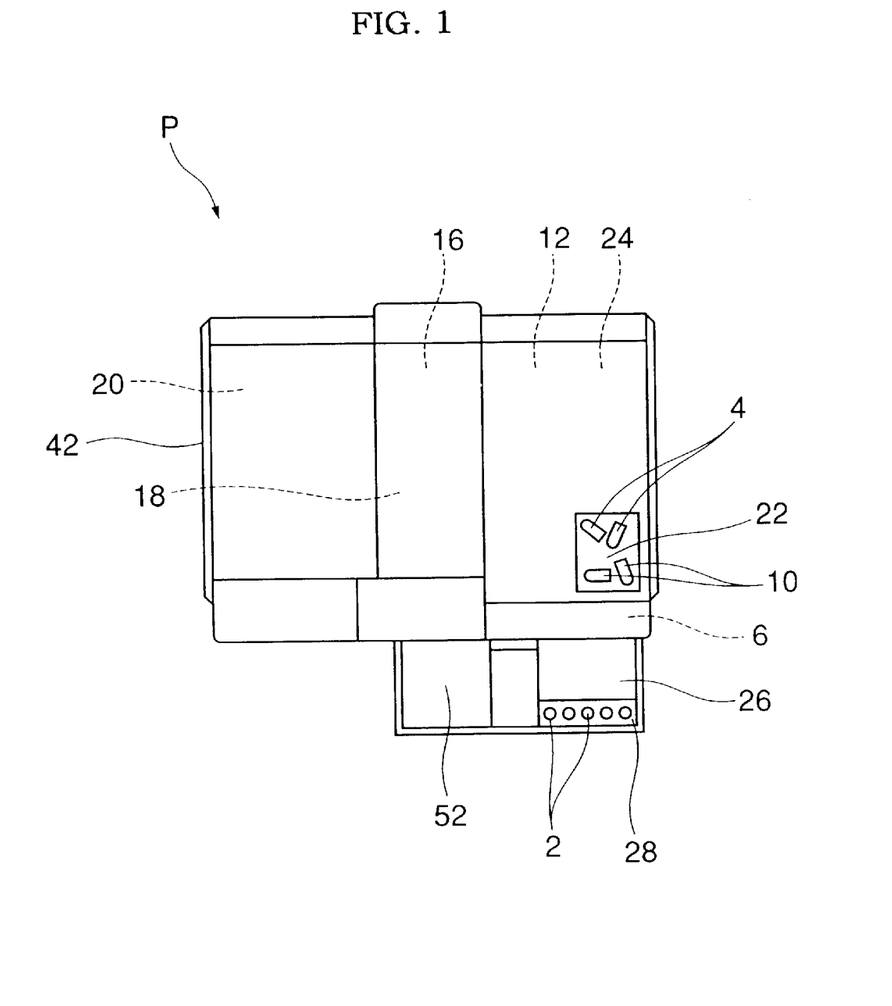
FIG. 1 is a plan view of an automatic analytical instrument in accordance with one embodiment of the invention.
Figure 2:
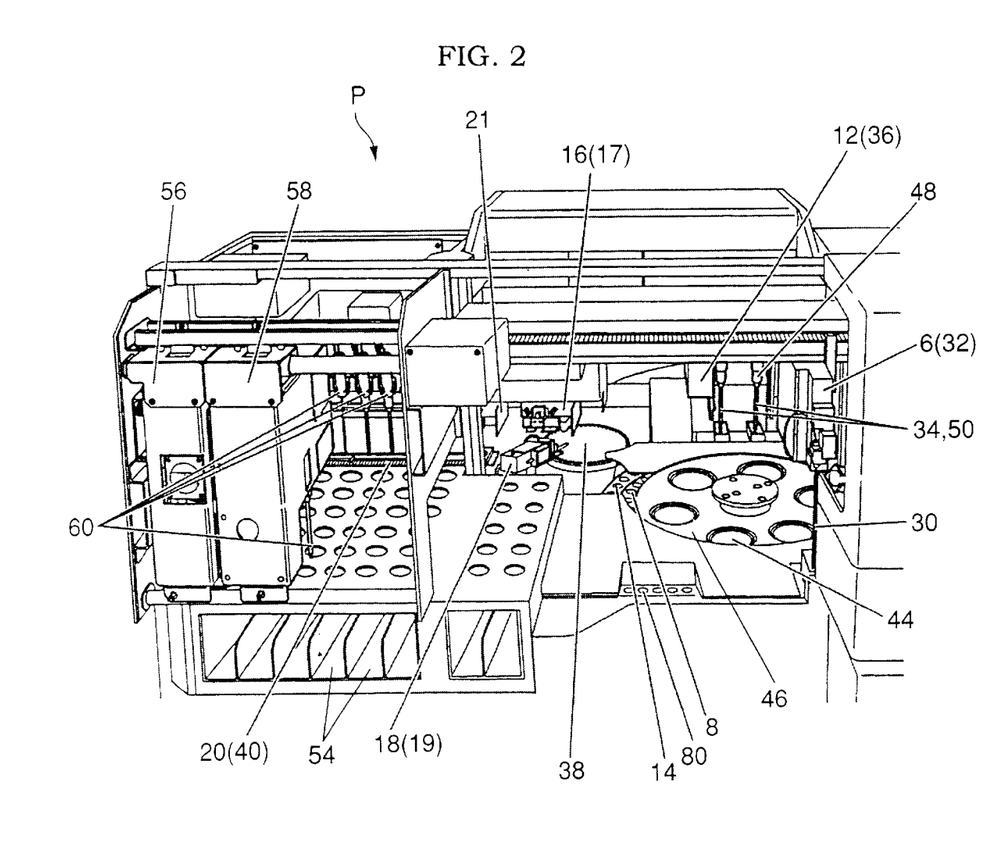
FIG. 2 is a perspective view showing an internal constitution of the automatic analytical instrument shown in FIG. 1.
Figure 3:
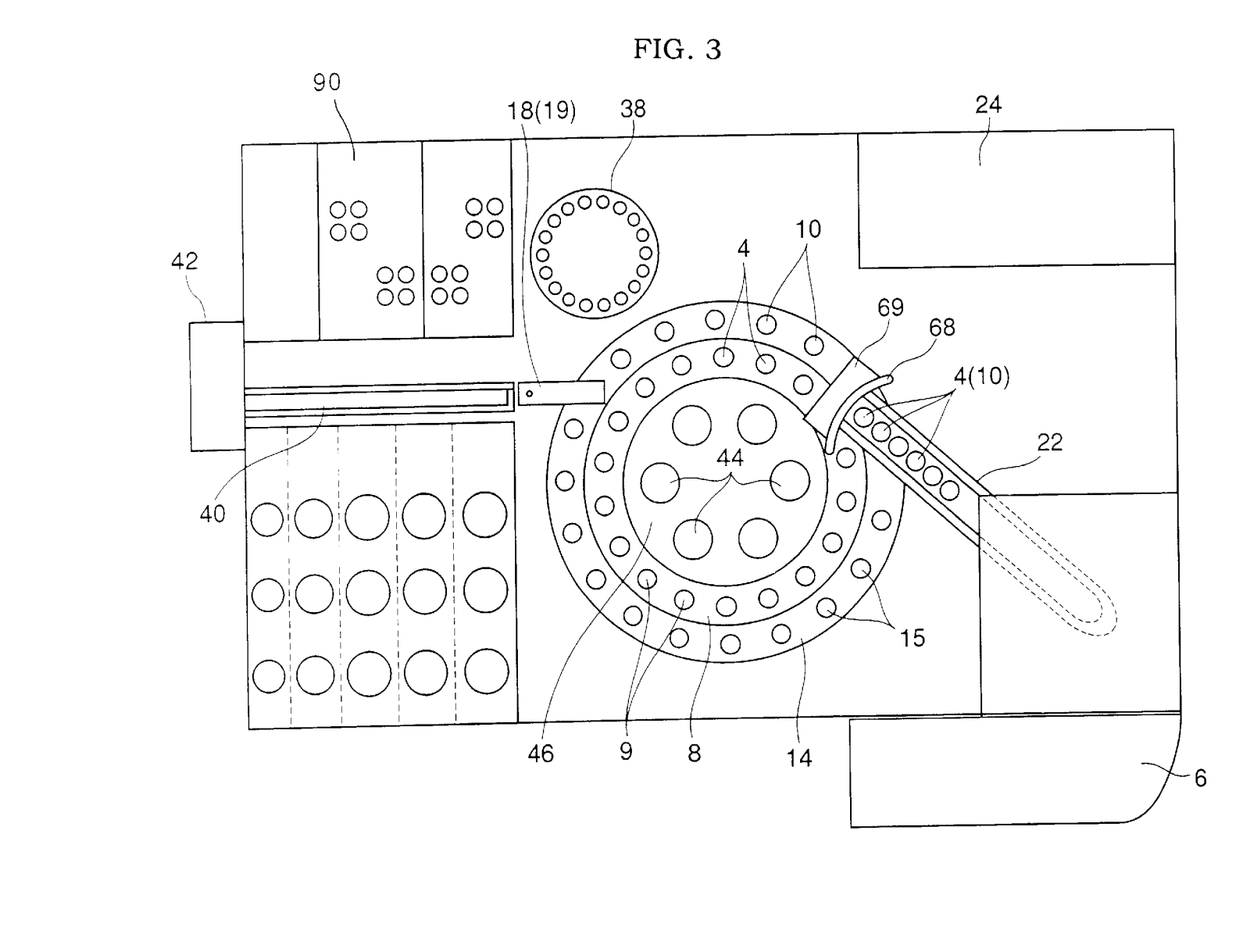
FIG. 3 is a plan view showing an internal constitution of the automatic analytical instrument shown in FIG. 1.
Figure 4:
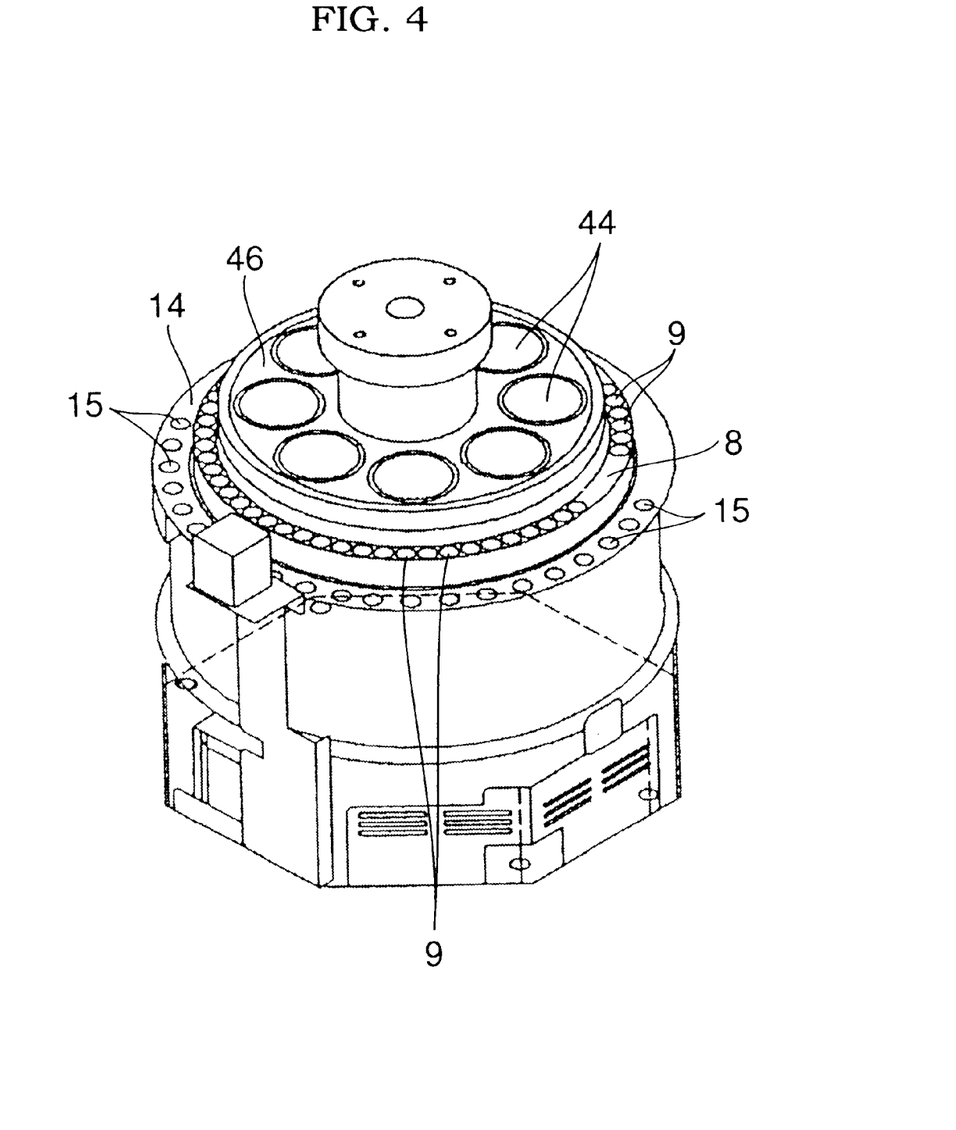
FIG. 4 is a perspective view of a first, a second and a third turning tables constituting the automatic analytical instrument shown in FIG. 1.

A sampler left tank 52 is provided to the left of the sampler right tank 26. A sample rack 28 set in the sample right tank 26 is sent into the automatic analytical instrument P automatically. And after the dispensing of the specimen, sample rack 28 is fed out in the sampler left tank 52. In front of the first turning table 8, the second turning table 14 and the third turning table 46 a sample holder 80 for an emergency is set.

A rack set unit 54 is provided in the left part of the automatic analytical instrument P and a plurality of reagent racks can be set there. In each reagent rack, tubes containing reagents and calibrator controllers can be set appropriately.

Two arms for supplying reagents 56, 58 and four pipettes for supplying reagents 60 are provided in the upper part of the rack set unit 54.

The cuvettes 4, 10 used as the storage tube 4 and the analytical tube 10 can be set in the first turning table 8 and the second turning table 14 by a cuvette supply unit 22 that functions as the tube supply unit.

Figure 5:
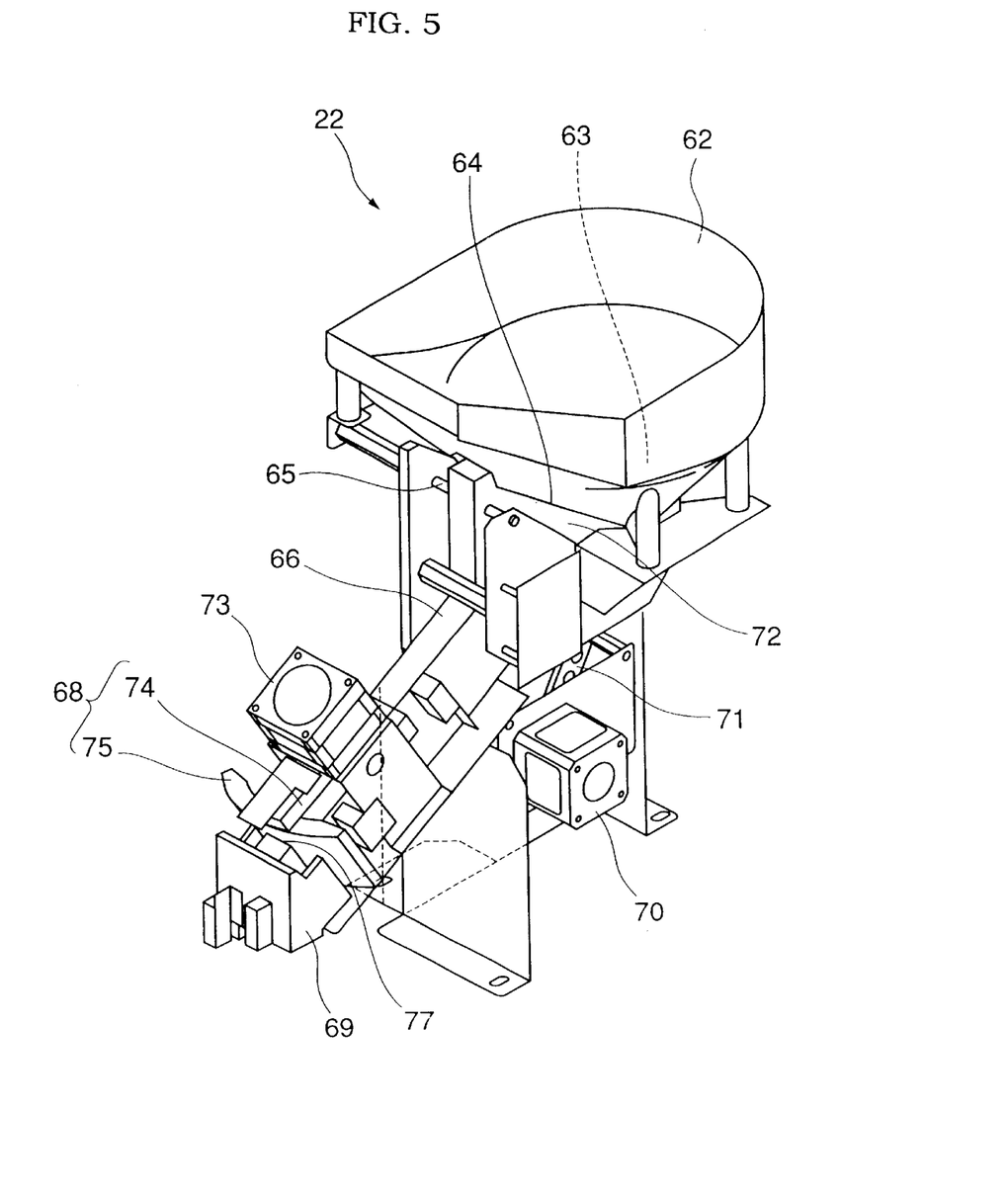
FIG. 5 is a perspective view of a tube supply unit constituting the automatic analytical instrument shown in FIG. 1.

As shown in FIG. 5, the cuvette supply unit 22 comprises a hopper 62 that serves as a storage part, a guide rail 64 and a shooter 66 that serve as a chute and the first guide body 68 and the second guide body 69 that serve as an allocation part.

The hopper 62 is a funnel having a hole for passing cuvette 63 in the lower part as a hole for passing tubes and stores a plurality of cuvettes 4, 10.

The guide rail 64 runs diagonally downwardly from the hole for passing cuvettes 63 in the hopper 62 and is capable of moving vertically. Explained in more detail, the guide rail 64 is supported by a swing member 72 so that it can move vertically. The swing member 72 is attached to a swing rod 71 whose one end is supported by a horizontal axis 65 and the other end is driven by a driving motor 70. The internal rail width of the guide rail 64 is larger than an external diameter of the main body of the cuvettes 4, 10 and smaller than the external diameter of the upper flange. The upper edge of the guide rail 64 appears and disappears from the hole for passing cuvettes 63 in the hopper 62 by the movements of the swing rod 71. The cuvettes 4, 10 in the hopper 62 are guided downwardly by the guide rail 64 and sent to the shooter 66 with the upper flange facing upwardly and the main body facing downwardly. The shooter 66 runs diagonally downwardly, connecting the lower end of the guide rail 64 and has the cuvettes 4, 10 sent from the guide rail 64 aligned and sliding down. The drive of the swing rod 71 is controlled by the control unit 24.

Figure 6:
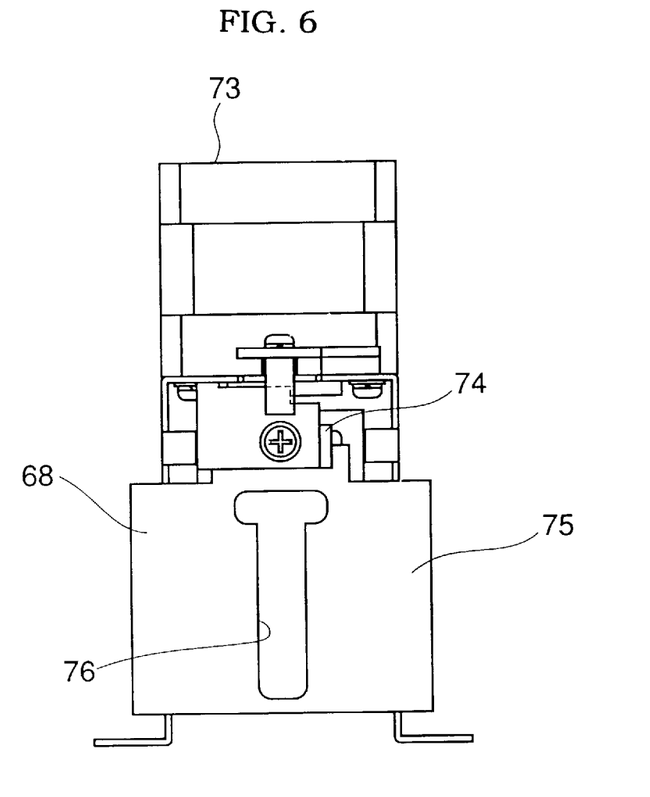
FIG. 6 is a front view showing a part of the tube supply unit shown in FIG. 5.
Figure 7:
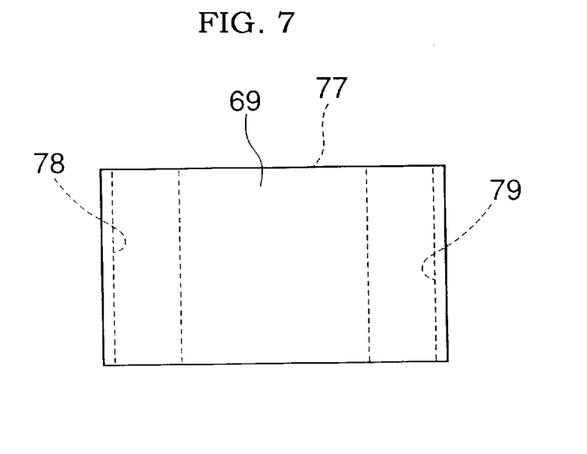
FIG. 7 is a front view showing another part of the tube supply unit shown in FIG. 5.

The first guide body 68 comprises a swing board 74 running upwardly along the lower part of the shooter 66 and is capable of moving from side to side, driven by a driving motor 73 and a curving guide board 75 attached to the lower end of the swing board 74. Shown in FIG. 6, a hole for passing cuvettes 76 is provided as a hole for passing tubes in the center of the guide board 75. This hole for passing cuvettes 76 is larger than the shape and the size of one cuvette 4, 10 seen from the front. The second guide body 69 is provided fixedly diagonally below the first guide body 68 and has a portion for holding cuvettes 77 in the center as a portion for holding tubes and a hole for dropping cuvettes 778, 79 on both sides, respectively, as a hole for dropping tubes. The drive of the swing board 74 is controlled by the control unit 24.

Figure 8:
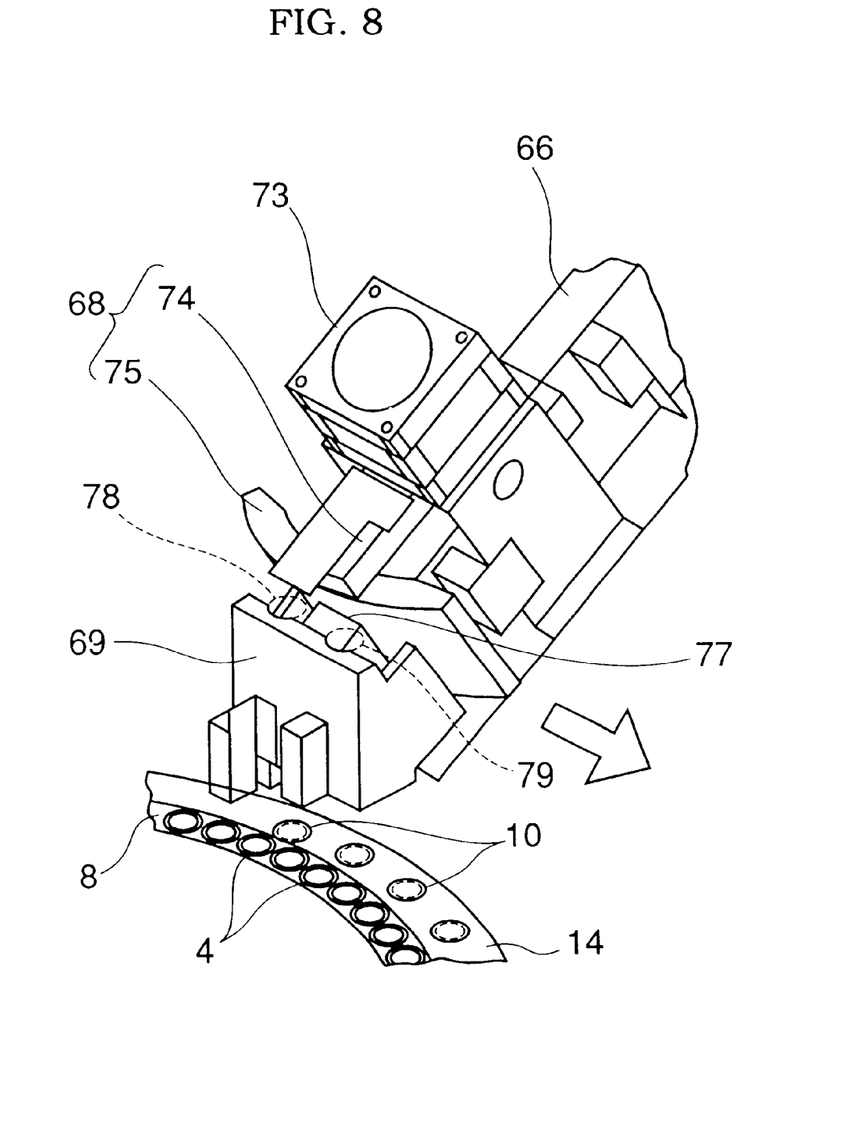
FIG. 8 is a perspective view showing a part of the tube supply unit shown in FIG. 5.

Shown in FIG. 8, the holes for dropping cuvettes 78,79 in the second guide body 69 are set just above the holding hole 9 in the first turning table 8 and the holding hole 15 in the second turning table 14.

Figure 9:
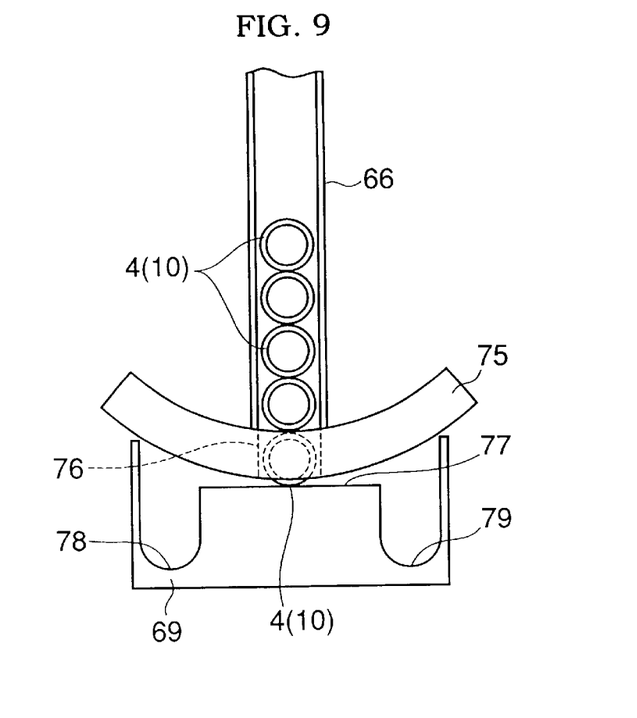
FIG. 9 is a plan view showing a state of a part of the tube supply unit shown in FIG. 5.
Figure 10:
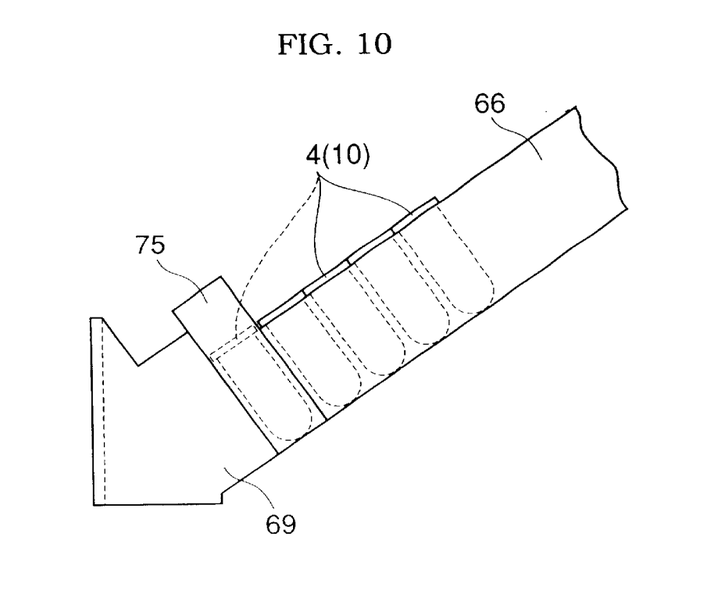
FIG. 10 is a side view showing a state of a part of the tube supply unit shown in FIG. 5.

Shown in FIG. 9 and FIG. 10, the first guide body 68 and the second guide body 69 hold a fore-running cuvette 4 (10) once, which has slid down the shooter 66 and partially passed the hole for passing cuvettes 76 in the guide board 75 with the portion for holding cuvettes 77 in the second guide body 69.

Figure 11:
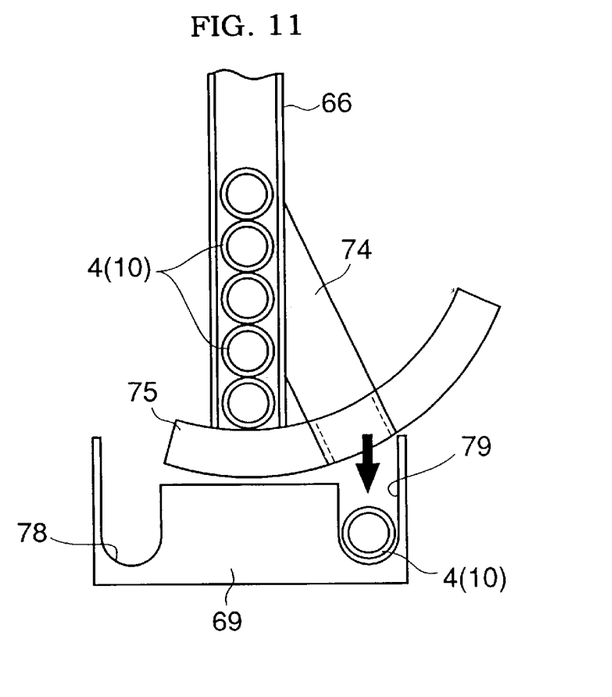
FIG. 11 is a plan view showing another state of a part of the tube supply unit shown in FIG. 5.
Figure 12:
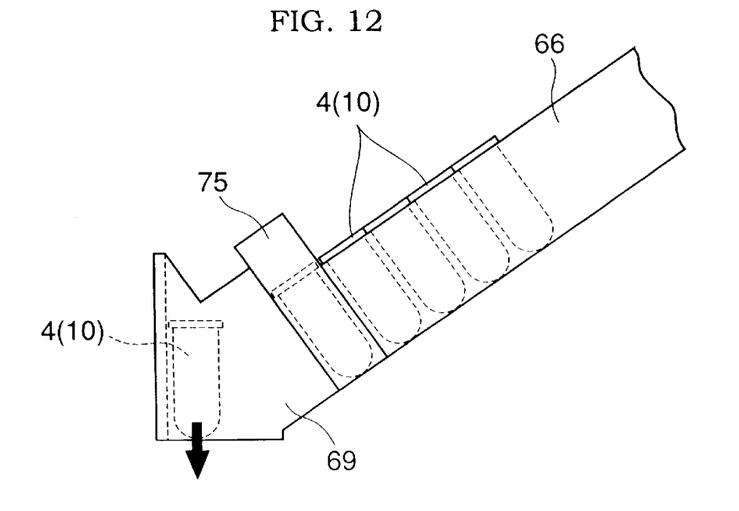
FIG. 12 is a side view showing another state of a part of the tube supply unit shown in FIG. 5.

Next, shown in FIG. 11 and FIG. 12, the swing board 74 and the connected guide board 75 vibrate to the right by the driving motor 73 and the hole for passing cuvettes 76 in the guide board 75 reaches the hole for dropping cuvettes 79 on the second guide body 69. The fore-running cuvette 4 (10) held falls on its own accord from the hole for passing cuvettes 76 in the guide board 75 through the hole for dropping cuvettes 79 in the second guide body 69 and is caught in the holding hole 9 in the first turning table 8 situated below and whose revolution is controlled by the control unit 24. On the other hand, when the swing board 74 and the connected guide board 75 swing to the left and the hole for passing cuvettes 76 in the guide board 75 reaches the left hole for dropping cuvettes 78 in the second guide body 69, the cuvette 4 (10) held in the forefront falls of its own accord from the hole for passing cuvettes 76 in the guide board 75 through the hole for dropping cuvettes 78 in the second guide body 69 and is caught in the holding hole 15 in the second turning table 14 situated below and whose revolution is controlled by the control unit 24.

Next, with reference to FIG. 1 and FIG. 2, an analytical flow of this automatic analytical instrument P is explained. Specimen plasma, which is in a specimen tube 2 that stands in the sample rack 28 placed in the sampler right tank 26, is sucked by the fist pipette 30, and is distributed by pouring into the cuvette (the storage tube) 4 set in the first turning table 8. The specimen sucked into the cuvette 4 is distributed by pouring again according to desired analytic items. Namely, for the items requiring a heated specimen, the specimen is distributed by pouring into the cuvette (the analytical tube) 10 set in the heated second turning table 14. For the rest, the specimen is distributed by pouring into the other cuvette 4 set in the non-heated first turning table 8. At that time, a diluted solution is distributed by pouring into it, if necessary. In the second turning table 14, preincuvation of the specimen contained in the cuvette 10 is conducted for a prescribed time. Next, a catcher 19 takes out the cuvette 10 containing the specimen. At this time, if necessary, reagent is added to it by reagent pipette 60. Then, the cuvette 10 is transferred to the heating table 38 and their preincuvation is conducted for a prescribed time. After a catcher 17 takes out the cuvette 10 containing the specimen and the reagent is added to it, the vibrating portion furnished in the catcher 17 vibrates the cuvette 10 and mixes the specimen. Next, the cuvette 10 is set in a prescribed hole in the photometry unit set at the back and to the left of the main body and analysis (measurement) is conducted. According to the order of analysis, when the analysis of the cuvette 10 is completed, the cuvettes 10 are conveyed onto the belt 40 by the catcher 21, and transported to the vent 42.

In this sequence, when the cuvettes 4, 10 in the first turning table 8 and the second turning table 14 are taken out, the control unit 24 orders the cuvette supply unit 22 to set the cuvettes 4, 10 selectively. The cuvettes 4, 10 are supplied simply by revolution of the first turning table 8 and the second turning table 14. In other words, the cuvette supply unit 22 can supply the cuvettes 4, 10 to the first turning table 8 and the second turning table 14 without moving. Also, this automatic analytical instrument P can separately control the pipettes 30, 34, 50, and 60, and arms 32, 36, 48, 56, and 58, which supply reagents or the cuvettes 4, 10 to each position and can realize high processing performance.

When the analytical result is beside the setting valve, a reflect test is conducted to set a predetermined re-measuring item and other related analytical item automatically. The specimen is distributed by pouring again from the cuvette 4 stored in the first turning table 8. Since the first turning table 8 is separate from the second turning table 14 that conducts preincuvation of the specimen, the specimen can be stored without being heated. If a reflect test is judged to be unnecessary, the cuvette 4 into which the specimen was distributed by pouring will be disposed of by the catcher 19.

What is claimed is:

1. An automatic analytical instrument comprising:
   a plurality of specimen tubes to store specimens;
   a plurality of storage tubes to store a part of the specimens contained in the specimen tubes by dispensing;
   a first dispensing unit to dispense the specimens contained in the specimen tubes into the storage tubes;
   a first turning table to hold a plurality of the storage tubes and transfer them by revolution;
   a plurality of analytical tubes to store a part of the specimens contained in the storage tubes by dispensing;
   a second dispensing unit to dispense the specimens contained in the storage tubes into the analytical tubes;
   a second turning table to hold a plurality of the analytical tubes and transfer them by revolution;
   an analytical unit to analyze the specimens contained in the analytical tubes;
   a transfer unit to transfer the analytical tubes held in the second turning table to the analytical unit;
   a delivering unit to deliver the analytical tubes after analysis is completed;
   a tube supply unit to supply the storage tubes and the analytical tubes to the first turning table and the second turning table, the tube supply unit including means for transporting the tubes to the first and second turning tables where the tubes are permitted to drop naturally into suitable retaining means in the respective first and second turning tables; and
   a control unit to control dispensing by the first dispensing unit and the second dispensing unit, revolution by the first turning table and the second turning table, analysis by the analytical unit, transfer by the transfer unit, delivery by the delivering unit, and supply by the tube supply unit.

2. An automatic analytical instrument as set forth in claim 1, wherein the storage tubes and the analytical tubes are identical and comprise disposable plastic tubes.

3. An automatic analytical instrument as set forth in claim 1, wherein the first turning table and the second turning table have a plurality of holding holes on their circumferences, respectively, to hold the storage tubes and the analytical tubes.

4. An automatic analytical instrument as set forth in claim 1, wherein the first turning table and the second turning table are set in concentric circles having different diameters.

5. An automatic analytical instrument as set forth in claim 1, wherein the tube supply unit comprises a storage part to store a plurality of the storage tubes and/or the analytical tubes, a chute that is set below the storage part and makes the tubes in the storage part align and slide down, and an allocation part that is set below the chute and hold the tubes sliding down the chute for the time being and then supply them to the first turning table and/or the second turning table into which they fall naturally.

6. An automatic analytical instrument as set forth in claim 5, wherein the storage part comprises a hopper having a hole for passing tubes in its lower part, the chute comprises a guide rail that runs diagonally downward from the hole for passing tubes in the hopper and that can swing up and down, and a shooter that runs diagonally downward and connects the lower part of this guide rail, and the allocation part comprises the first guide body set diagonally below the shooter, which can swing from side to side and has a hole for passing tubes in the center, and the second guide body set diagonally below the first guide body fixedly, which has a portion for holding tubes in the center and a hole for dropping tubes, respectively, in the sides.

7. An automatic analytical instrument as set forth in claim 6, wherein the control unit further controls the swing of the guide rail and the swing of the first guide body.

8. An automatic analytical instrument, as set forth in claim 1, further comprising:
   a third turning table which holds a plurality of reagent storage tubes for the purpose of storing various reagents, and transfers them by revolution.

9. An automatic analytical instrument as set forth in claim 8, wherein the first, second and the third turning tables are placed in concentric circles having different diameters.

10. An automatic analytical instrument as set forth in claim 8, further comprising:
   a heating/cooling unit that heats and/or cools at least one of the first, the second and the third turning tables and a control unit further controls said heating/cooling unit.

* * * * *